United States Patent
Walsworth et al.

(10) Patent No.: US 9,157,859 B2
(45) Date of Patent: Oct. 13, 2015

(54) EFFICIENT FLUORESCENCE DETECTION IN SOLID STATE SPIN SYSTEMS

(75) Inventors: Ronald Walsworth, Newton, MA (US); David Lesage, Boston, MA (US)

(73) Assignee: PRESIDENT AND FELLOWS OF HARVARD COLLEGE, Cambridge, MA (US)

( * ) Notice: Subject to any disclaimer, the term of this patent is extended or adjusted under 35 U.S.C. 154(b) by 52 days.

(21) Appl. No.: 14/125,068

(22) PCT Filed: Jun. 13, 2012

(86) PCT No.: PCT/US2012/042271
§ 371 (c)(1),
(2), (4) Date: Mar. 7, 2014

(87) PCT Pub. No.: WO2012/174125
PCT Pub. Date: Dec. 20, 2012

(65) Prior Publication Data
US 2014/0166904 A1   Jun. 19, 2014

Related U.S. Application Data

(60) Provisional application No. 61/496,464, filed on Jun. 13, 2011.

(51) Int. Cl.
*G01N 21/64* (2006.01)
*G01R 33/12* (2006.01)

(52) U.S. Cl.
CPC .......... *G01N 21/645* (2013.01); *G01N 21/6489* (2013.01); *G01R 33/1284* (2013.01)

(58) Field of Classification Search
CPC ............ G01N 21/6458; G01N 21/645; G01N 21/6489; G01R 33/1284
See application file for complete search history.

(56) References Cited

U.S. PATENT DOCUMENTS

| | | |
|---|---|---|
| 2006/0234419 A1 | 10/2006 | Linares et al. |
| 2010/0308813 A1 | 12/2010 | Lukin et al. |

(Continued)

FOREIGN PATENT DOCUMENTS

| | | |
|---|---|---|
| JP | 61-207951 A | 9/1986 |
| JP | 63-502052 A | 8/1988 |

(Continued)

OTHER PUBLICATIONS

Office Action for Japanese Patent Application No. 2014-515960, JPO (Japanese Patent Office), Dec. 15, 2014.

(Continued)

*Primary Examiner* — Yara B Green
(74) *Attorney, Agent, or Firm* — Elizabeth Kim Patent Law Offices LLC

(57) ABSTRACT

Efficient fluorescence detection is achieved by optically guiding fluorescence light generated by color centers within a sample to photodetectors outside the sample. A fluorescence detection system may use a sample containing one or more fluorescence color centers that emit fluorescent light when irradiated with excitation light from an optical source. The sample has an index of refraction greater than its surrounding medium. The sample may include one or more output faces and further include at least two opposing faces configured to internally reflect the fluorescent light emitted by the fluorescent color centers, and to optically guide the emitted fluorescent light to the one or more output faces. The fluorescence detection system may include one or more optical detector configured to receive fluorescent light emitted through the one or more output faces, and a microwave source configured to manipulate the electronic spin of the fluorescent color centers.

25 Claims, 5 Drawing Sheets

(56) References Cited

U.S. PATENT DOCUMENTS

| | | | |
|---|---|---|---|
| 2011/0062957 A1* | 3/2011 | Fu et al. | 324/307 |
| 2012/0019242 A1* | 1/2012 | Hollenberg et al. | 324/300 |
| 2014/0037932 A1* | 2/2014 | Twitchen et al. | 428/220 |
| 2014/0077231 A1* | 3/2014 | Twitchen et al. | 257/77 |

FOREIGN PATENT DOCUMENTS

| | | |
|---|---|---|
| JP | 2002-214194 A | 7/2002 |
| WO | 2009073736 A1 | 11/2009 |
| WO | 2010010352 A1 | 1/2010 |

OTHER PUBLICATIONS

Taylor JM et al, "High-sensitivity diamond magnetometer with nanoscale resolution", Internet Citation, XP007908377, pp. 1-29, May 8, 2008. Retrieved from the Internet: URL:http://arxiv.org/PS_cache/arxiv/pdf/0805/0805.1367v1.pdf [retrieved on Apr. 28, 2009].

J. R. Maze et al, "Nanoscale magnetic sensing with an individual electronic spin in diamond", Nature, vol. 455, No. 7213, pp. 644-647, Oct. 2, 2008.

Hadden J. et al, "Strongly enhanced photon collection from diamond defect centers under microfabricated integrated solid immersion lenses," Applied Physics Letters, vol. 97, No. 24, p. 241901, American Institute of Physics, Melville, NY, US, Dec. 13, 2010.

Siyushev P. et al, "Monolithic diamond optics for single photon detection", Applied Physics Letters, vol. 97, No. 24, p. 241902, American Institute of Physics, Melville, NY, US, Dec. 13, 2010.

F. Dolde et al, "Electric-field sensing using single diamond spins", Nature Physics, vol. 7, No. 6, pp. 459-463, Jun. 1, 2011.

D. Le Sage et al, "Efficient photon detection from color centers in a diamond optical waveguide", Physical Review B., vol. 85, No. 12, Mar. 1, 2012.

"International Search Report" for PCT/US2012/042271, 3 pages, European Patent Office, Rijswik, The Netherlands, Sep. 5, 2012.

* cited by examiner

EFFICIENT FLUORESCENCE DETECTION IN SOLID STATE SPIN SYSTEMS

CROSS-REFERENCE TO RELATED APPLICATIONS

This application is a 35 U.S.C. §371 National Phase Entry Application of International Application no. PCT/US12/42271 filed Jun. 13, 2012, which designates the U.S., and which claims the benefit of priority under 35 U.S.C. §119(e) of U.S. Provisional Patent Application No. 61/496,464 (the "'464 provisional application"), filed Jun. 13, 2011 and entitled "Fluorescence Detection Using Total Internal Reflection As Light Guide." The contents of each of these applications are incorporated herein by reference in their entireties.

STATEMENT REGARDING FEDERALLY SPONSORED RESEARCH

This invention was made with government support under contract number 60NANB10D002 awarded by NIST (National Institute Of Standards And Technology). The government has certain rights in the invention.

BACKGROUND

A variety of fluorescent point defect centers in diamond have been identified that have potential applications in fields that include quantum information and biological imaging. In particular, the negatively charged nitrogen-vacancy (NV) center has attracted much interest. Demonstrated applications of NV centers include, without limitation, quantum information processing, super-resolution microscopy, Nano scale magnetometer using a single NV, and vector magnetic field imaging using ensembles of NVs.

For all of these applications, the photon collection efficiency is critically important.

Conventional methods of fluorescence detection typically result in photon collection efficiencies $\eta_c$ of only about 10% or less. For example, a common limitation of experiments using color centers in diamond is the poor photon collection efficiency of microscope objectives due to refraction at the diamond interface. When detector coupling and quantum efficiencies are taken into account, photon detection efficiencies $\eta_d$ of 2% or less are typical.

BRIEF DESCRIPTION OF THE DRAWINGS

The drawings disclose illustrative embodiments. They do not set forth all embodiments. Other embodiments may be used in addition or instead.

DETAILED DESCRIPTION

Illustrative embodiments are discussed in this application. Other embodiments may be used in addition or instead.

It should be understood that the invention is not limited to the particular embodiments described, as such may vary. Also, the terminology used herein is for the purpose of describing particular embodiments only, and is not intended to be limiting, since the scope of the present invention will be limited only by the appended claims.

Where a range of values is provided, each intervening value, to the tenth of the unit of the lower limit unless the context clearly dictates otherwise, between the upper and lower limit of that range and any other stated or intervening value in that stated range is encompassed within the invention. The upper and lower limits of these smaller ranges may independently be included in the smaller ranges is also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, a limited number of the exemplary methods and materials are described herein.

Figure 1:
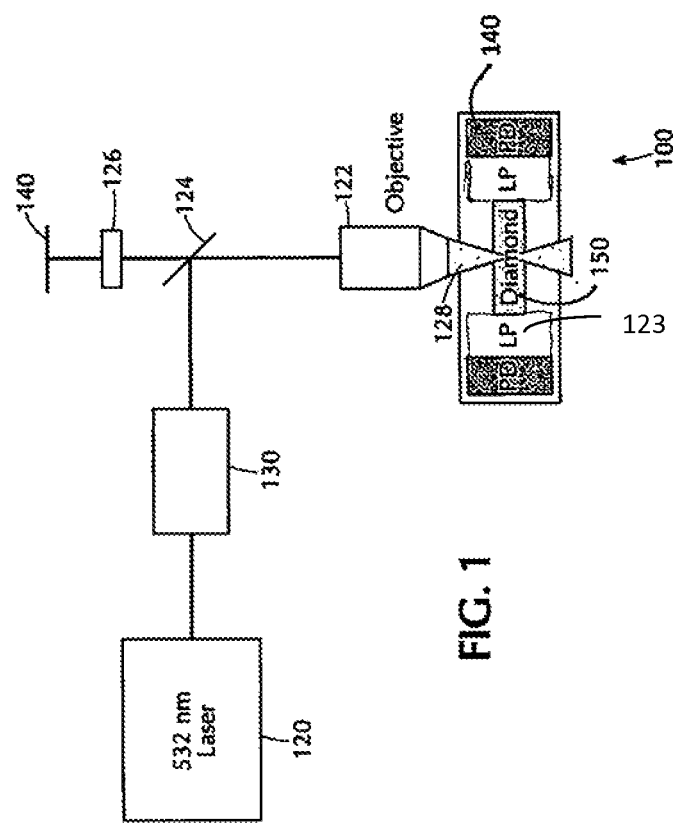
FIG. 1 is a schematic block diagram of a fluorescence detection system in accordance with one or more embodiments of the present application.

In the present disclosure, methods and systems are described that can realize high optical detection efficiencies for color center fluorescence in solid state spin samples such as diamond. These methods and systems rely upon internal reflection to optically guide the fluoresced photons to one or more detectors outside the sample FIG. 1 is a schematic block diagram of a fluorescence detection system 100 in accordance with one or more embodiments of the present application. In the illustrated system 100, a sample 150 is used that is formed of diamond material and contains NV fluorescence color centers. The sample 150 has an index of refraction substantially greater than its surrounding medium, i.e. air. Thus fluorescent light emitted by the color centers can be internally reflected from the inner surfaces of the diamond, via either total or internal reflection, so that the diamond can act as an optical waveguide.

Figure 3A:
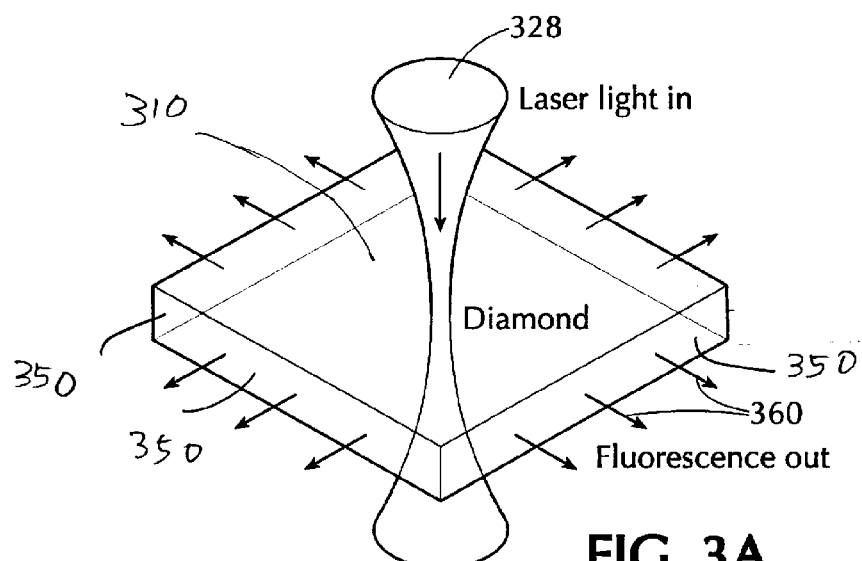
FIG. 3A schematically illustrates fluorescence side-collection in accordance with one or more embodiments of the present disclosure.
Figure 3B:
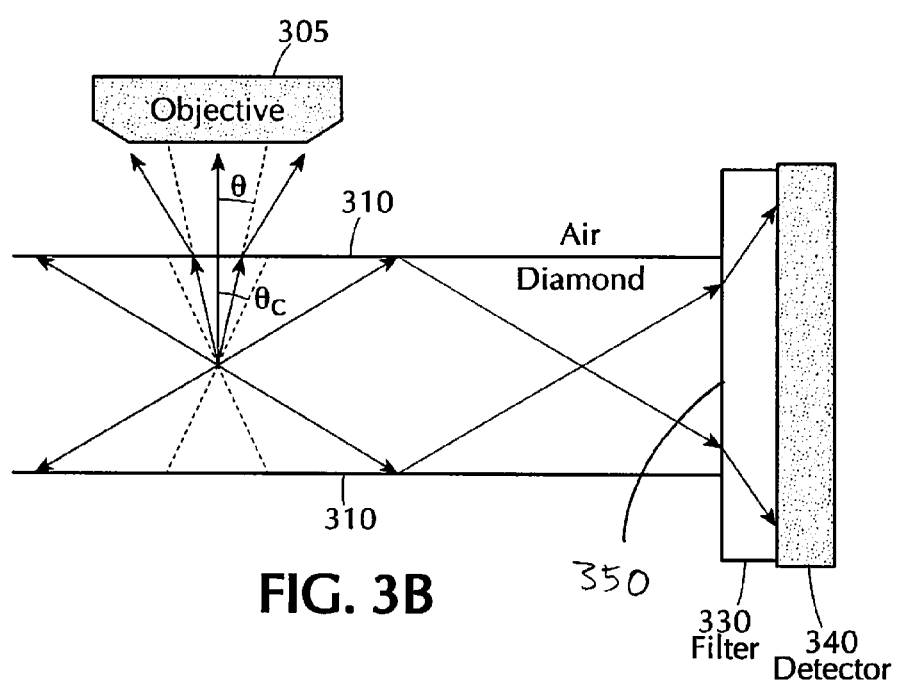
FIG. 3B provides ray diagrams illustrating refraction at the diamond surface and light guided by total internal reflection above the critical angle C.

As seen more clearly from FIGS. 3A and 3B, the sample includes at least one output face, and at least two opposing faces configured to internally reflect the fluorescent light emitted by the one or more fluorescent color centers and optically guide the emitted fluorescent light to the output face.

The system 100 further includes an optical source 120 configured to generate excitation light that causes emission of fluorescent light from the color centers when applied thereto. In the illustrated embodiment, the optical source 120 is a 532-nm excitation laser. Many other kinds of optical sources can be used. For example, the optical source may be a laser or an LED tunable to a wavelength less than 637 nm.

The system 100 further includes at least one optical detector 140 configured to receive the fluorescent light that is emitted by the color centers, internally reflected from opposing surfaces of the diamond sample, and exits through one or more output faces of the diamond sample 150. The detector may be positioned in contact with the output face either directly, or indirectly via a filter.

In some embodiments, a plurality of detectors may be provided, each detector configured to receive light from an associated output face of the detector.

In some embodiments, the detector may have a size and position relative to the output faces to receive at least 75% of fluorescent light emitted through the output face.

In some embodiments, the system 100 may also include an objective 122 that focuses light from the laser onto the sample 150, and one or more dichroic mirrors 124 that separates the fluorescence from the excitation beam, and a fast-switching AOM (acousto-optic modulator) 130 that pulses the laser 120 with precise timing. In one or more embodiments, one or more of the optical filters 123 may be placed in contact with the output edges of the diamond sample 150. The filters 123 may be 650 nm long-pass filters, for example, and may be configured to transmit most of the NV fluorescence band (637-800 nm), while reflecting scattered 532-nm light used to excite the NVs.

Photodiodes 140 may be affixed to the backs of the filters. The filters may be chip-style Si photodiodes, for example, and may be disposed on a 2-mm-thick quartz substrate having a thickness of about 2 mm. To maximize the detection acceptance angle, large active-area photodiodes, for example having an area of about 6 mm×7 mm, may be employed. In other embodiments, smaller detectors with thinner optical filters may be used.

A processing system may be integrated with the system 100. The processing system is configured to implement the methods, systems, and algorithms described in the present application. In particular, the processing system may be configured to determine information about an external field based on the fluorescent light received by the optical detector 140. The external field may include without limitation an electric field or a magnetic field.

The processing system may include, or may consist of, any type of microprocessor, Nano processor, microchip, or Nano chip. The processing system may be selectively configured and/or activated by a computer program stored therein. It may include a computer-usable medium in which such a computer program may be stored, to implement the methods and systems described above. The computer-usable medium may have stored therein computer-usable instructions for the processing system. The methods and systems in the present application have not been described with reference to any particular programming language; thus it will be appreciated that a variety of platforms and programming languages may be used to implement the teachings of the present application.

Figure 2:
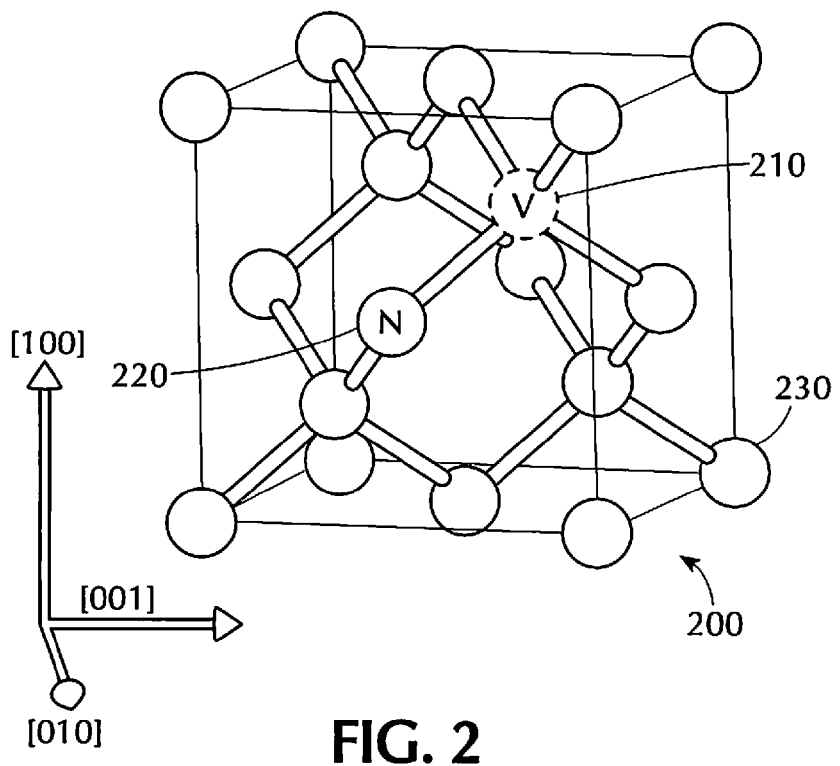
FIG. 2 illustrates an NV center consisting of a substitution nitrogen atom neighboring a lattice vacancy.

FIG. 2 illustrates an NV center consisting of a substitution nitrogen atom N adjacent to a lattice vacancy 210, i.e. the NV center is an empty position or vacancy resulting from a missing carbon atom in the diamond lattice. The NV impurity is based in the lattice of carbon atoms 230, where two adjacent sites are altered, because one carbon atom is replaced with a nitrogen atom 220 and the other space is left vacant.

In some embodiments, the sample 150 may be a diamond chip oriented along the [100] axis, and may have a size of about 4.3 mm×4.3 mm×0.2 m. The sample 150 may be grown via CVD (chemical vapor deposition) with a high NV density, on the order of about $10^{15}$ cm.$^{-3}$ One particular implementation of the internal reflection guided system described above is a method referred to as side-collection. FIGS. 3A and 3B schematically illustrate fluorescence side-collection in accordance with one or more embodiments of the present application.

As seen in FIGS. 3A and 3B, in the side collection method a focused laser beam 328 is used to excite color centers in a specific volume within the sample, and much of the resulting fluorescence 360 is detected after it is optically guided through the sample via internal reflection from at least two opposing faces 310 of the sample and exits one or more output faces 350 of the diamond waveguide.

In some embodiments, the two opposing faces 310 may be parallel to within 10°.

In some embodiments, the sample may be in the form of a plate, the plate's major faces forming the opposing faces for optically guiding the emitted fluorescent light. The plate may include one or more side faces 350 that form the output faces.

In some embodiments, a plurality of detectors may be provided, each detector configured to receive light from an associated side face of the detector. Thus in the embodiment illustrated in FIG. 3A, four photo detectors may be arranged around the four primary sides of the diamond chip. In other embodiments, the number of detectors may be reduced, for example if one or more outer surfaces of the sample are polished and mirror coated.

In some embodiments, the sample 310 may have a rectangular solid configuration, with opposing internal surfaces that are substantially planar and substantially parallel to each other.

Conventionally, photons emitted from NVs in a bulk diamond substrate are collected using a microscope objective with a large NA (numerical aperture). However, refraction at the flat diamond interface reduces the effective NA of the objective by a factor equal to the refractive index of diamond ($n_d$=2.4), resulting in a photon collection efficiency $\eta_c$ of about 10%, assuming a maximum objective NA of 1.49. Photon detection efficiencies $\eta_d$<2% are typical when detector coupling and quantum efficiencies are taken into account.

It has been found that about 91% of NV fluorescence is emitted into angles exceeding the critical angle (25°), and is totally internally reflected, as further described below. 50% exits the side edges of a rectangular solid sample, upon reaching the sides. More exits the sides after multiple scatterings. By placing one or more detectors at the side edges of the diamond, the collection efficiency is expected to be in the range of 50%<$\eta$<90%, as further described below. The side collection method is thus ideal for large-volume ensemble NV measurements because light can be efficiently detected from anywhere inside the diamond.

The expected efficiency of the above-described side-collection method described above can be estimated using theoretical models of the average NV emission pattern and realistic approximations of the diamond chip geometry and acceptance angles of the detectors. It was found that ≈91% of the NV fluorescence is confined by TIR between the polished (100) planar surfaces of the diamond chip, and ≈29% reaches the detectors on first incidence of the photons with the side edges of the diamond chip. Much of the light also undergoes TIR off the sides, but may reach the detectors after many reflections within the diamond. We therefore expect 29%<$\eta$<91% for the side-collection technique, Depending on criteria such as details of the experimental geometry and diamond chip surface properties, the collection efficiency $\eta_c$ is therefore expected to be between about 29% to about 91%.

Figure 4:
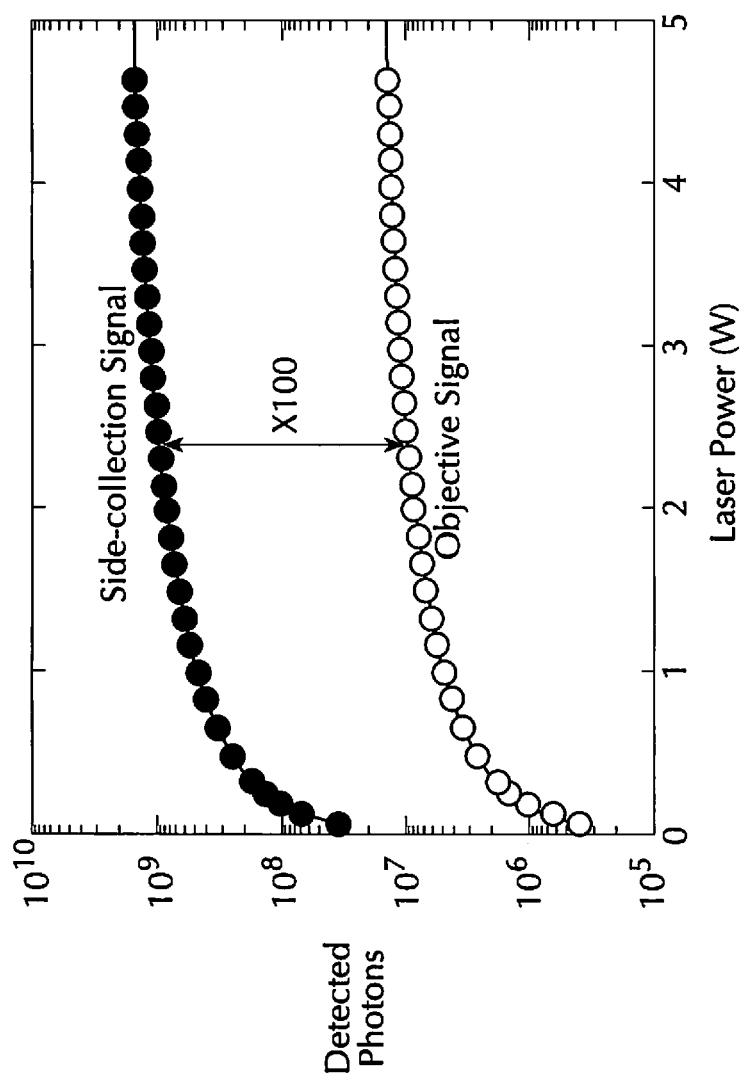
FIG. 4 compares NV fluorescence signals detected by the side-collection method to NV fluorescence signals detected using a microscope objective.

FIG. 4 compares the NV fluorescence signal (number of detected photons) detected by the side-collection method, as compared to the NV fluorescence signal detected using a microscope objective. In particular, FIG. 4 compares the integrated number of fluorescence photons detected with the two respective collection modalities, namely side collection and microscope objective, during a 300-ns duration pulse of 532- nm excitation laser light, at various laser powers. In FIG. 4, the integrated photon count was measured by alternately connecting a charge-sensitive amplifier to the photodiode(s) of the two collection paths, and recording the average signal amplitude. As illustrated in FIG. 4, the side-collection signal was found to have a 100±5 times larger photon count than the microscope objective signal, under identical experimental conditions.

In some embodiments, the methods and systems described above can be applied to measurement of static and periodic magnetic fields, i.e. DC and AC magnetometer, for example sensitive magnetometer that uses ensembles of NV spins in a diamond chip.

By way of example, in one embodiment standard spin-echo techniques may be used on a sample that includes approximately ~108 NVs contributing to a magnetometer signal in a ~$10^{-4}$ mm$^3$ laser excitation volume. In overview, in this embodiment, optical pump pulses can be applied to the NV spins to prepare them in the $|m_s=0\rangle$ state. A subsequent microwave spin-echo sequence allows the NV spins to probe an applied 20-kHz magnetic field. An optical readout pulse allows measurement of the change in NV spin-dependent fluorescence compared to the initial state.

In an exemplary embodiment, a 37.5-G static magnetic field may be applied in the direction of the [111] axis (illustrate in FIG. 2), so that an applied microwave field can be used to resonantly select $|m_S=0\rangle \leftrightarrow |m_S=1\rangle$ spin transitions of the [111]-oriented NVs. In this way, one-quarter of the total number of NV spins are resonantly manipulated, since NV orientations are distributed equally among the four crystallographic axes. By sweeping the spin-echo duration (τ), a $T_2$ coherence curve can be generated, with revivals at even multiples of the $^{13}$C nuclear precession period. For the high NV-density diamond sample described above, the extracted value of $T_2$ was 35 μs. An AC magnetometer curve can then be generated by varying the amplitude of a 20-kHz AC magnetic field, with τ=50 μs.

Figure 5:
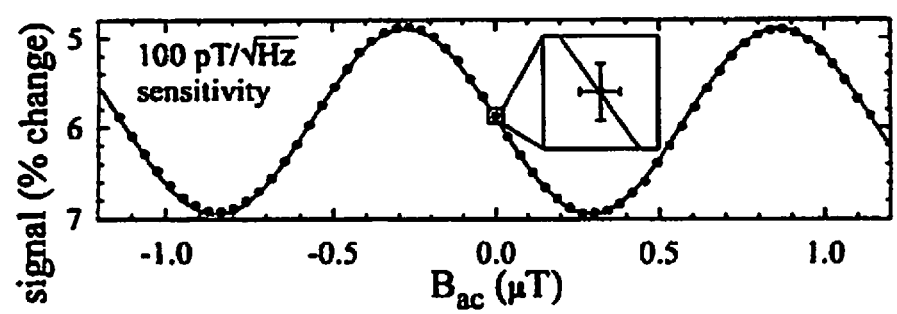
FIG. 5 illustrates an AC magnetometer curve generated in a magnetometer application that uses fluorescence side-collection, in accordance with one embodiment of the present application.

FIG. 5 illustrates the AC magnetometer curve generated in the above-described magnetometer application that uses fluorescence side-collection. As explained above, the NV-diamond AC magnetometer curve shown in FIG. 5 is produced by varying $B_{ack}$ with τ=50 as produces. In FIG. 5, the zoomed-in region of the curve near $B_{ack}$=0 depicts the mean and standard deviation of a large number of AC magnetometer measurements, each lasting 57 μs. The ±0.071% uncertainty in the signal (vertical error bars) corresponds to a ±13 not uncertainty in $B_{ack}$ (horizontal error bars) for a single measurement. The curve shown in FIG. 5 thus yields a magnetometer sensitivity η of about 100 pT (picotesla)/√Hz. In this embodiment, the sensitivity was limited by laser and electrical noise. Expected shot-noise limited sensitivity was 4 pT/√Hz.

Further improvements in AC magnetometer sensitivities, to about 1 pt./√Hz or more, my be achieved. Shot-noise limited measurements are expected to be performed. Also, higher sensitivities may be attained by using larger NV ensembles, i.e. further increasing the sample volume that is probed by the laser compared to the current measured volume of $10^5$ μm$^3$. Higher sensitivities should be possible with larger NV ensembles. Also, better diamond samples, for example isotopic ally engineered $^{12}$C samples and/or samples with high N→NV conversion, together with environment decoupling techniques, may make sub –pT/√Hz magnetometry possible. While AC magnetometry sensitivity has been described in conjunction with FIG. 5, the fluorescence detection methods and systems described in this application are also applicable to DC magnetometry, i.e. to the sensing of static or DC magnetic fields.

In summary, methods and systems have been described for achieving efficient optical detection for color center fluorescence in spin samples such as diamond, by using the large refractive index of the spin sample and resultant total internal reflection to guide the color center fluorescence light to detectors placed near outer edges of the sample. The methods and systems described in this application are applicable to both single and ensemble color center fluorescence measurements, and to spatially-resolved measurements.

The photon detection enhancement resulting from the methods and systems described above has many other potential applications. By way of example, magnetometry may be extended to magnetic field imaging by using a thin layer of NVs near the diamond chip surface by scanning the laser focus while making time-resolved side-collection fluorescence measurements. The high SNR provided by side collection also greatly increases the speed of NV ensemble measurements, which may be used to study decoherence processes and develop NV spin manipulation protocols for magnetometry and quantum information.

The components, steps, features, objects, benefits and advantages that have been discussed are merely illustrative. None of them, nor the discussions relating to them, are intended to limit the scope of protection in any way. Numerous other embodiments are also contemplated, including embodiments that have fewer, additional, and/or different components, steps, features, objects, benefits and advantages. The components and steps may also be arranged and ordered differently.

Nothing that has been stated or illustrated is intended to cause a dedication of any component, step, feature, object, benefit, advantage, or equivalent to the public. While the specification describes particular embodiments of the present disclosure, those of ordinary skill can devise variations of the present disclosure without departing from the inventive concepts disclosed in the disclosure.

While certain embodiments have been described, it is to be understood that the concepts implicit in these embodiments may be used in other embodiments as well. In the present disclosure, reference to an element in the singular is not intended to mean "one and only one" unless specifically so stated, but rather "one or more." All structural and functional equivalents to the elements of the various embodiments described throughout this disclosure, known or later come to be known to those of ordinary skill in the art, are expressly incorporated herein by reference.

What is claimed is:

1. A fluorescence detection system comprising:
   an optical source configured to generate excitation light;
   a sample containing one or more fluorescence color centers that emit fluorescent light when irradiated with the excitation light from the optical source, wherein the sample has an index of refraction greater than its surrounding medium, said sample comprising at least one output face and further comprising at least two opposing faces configured to internally reflect the fluorescent light emitted by the one or more fluorescent color centers and optically guide the emitted fluorescent light to said at least one output face;
   at least one optical detector configured to receive fluorescent light emitted through said at least one output face; and
   a microwave source configured to manipulate electronic spin of the one or more fluorescent color centers;

wherein the sample is in the form of a plate, the plate major faces forming said at least two opposing faces for optically guiding the emitted fluorescent light and the plate further comprising one or more side faces forming said at least one output face; and wherein the two opposing faces are parallel to within 10°.

2. The fluorescence detection system of claim 1, wherein the sample is formed of diamond material.

3. The fluorescence detection system of claim 2, wherein the color centers comprise NV (nitrogen vacancy) centers in the diamond material.

4. A fluorescence detection system comprising:
an optical source configured to generate excitation light;
a sample containing one or more fluorescence color centers that emit fluorescent light when irradiated with the excitation light from the optical source, wherein the sample has an index of refraction greater than its surrounding medium, said sample comprising at least one output face and further comprising at least two opposing faces configured to internally reflect the fluorescent light emitted by the one or more fluorescent color centers and optically guide the emitted fluorescent light to said at least one output face;
at least one optical detector configured to receive fluorescent light emitted through said at least one output face; and
a microwave source configured to manipulate electronic spin of the one or more fluorescent color centers;
wherein the sample is in the form of a plate, the plate major faces forming said at least two opposing faces for optically guiding the emitted fluorescent light and the plate further comprising one or more side faces forming said at least one output face, and
wherein the plate comprises a plurality of side faces and the at least one optical detector is configured to receive fluorescent light emitted from at least two of said plurality of side faces.

5. The fluorescence detection system of claim 4, wherein a plurality of optical detectors are provided, each detector configured to receive light from an associated side face.

6. The fluorescence detection system of claim 4, wherein the sample is formed of diamond material.

7. The fluorescence detection system of claim 6, wherein the color centers comprise NV (nitrogen vacancy) centers in the diamond material.

8. A fluorescence detection system comprising:
an optical source configured to generate excitation light;
a sample containing one or more fluorescence color centers that emit fluorescent light when irradiated with the excitation light from the optical source, wherein the sample has an index of refraction greater than its surrounding medium, said sample comprising at least one output face and further comprising at least two opposing faces configured to internally reflect the fluorescent light emitted by the one or more fluorescent color centers and optically guide the emitted fluorescent light to said at least one output face;
at least one optical detector configured to receive fluorescent light emitted through said at least one output face; and
a microwave source configured to manipulate electronic spin of the one or more fluorescent color centers;
wherein said at least one optical detector has a size and position relative to said at least one output face to receive at least 75% of fluorescent light emitted through said at least one output face.

9. The fluorescence detection system of claim 8, wherein the optical source is a laser or LED tunable to a wavelength of less than 637 nm.

10. The fluorescence detection system of claim 8, wherein the color centers comprise NV (nitrogen vacancy) centers in diamond material and wherein the optical source is further configured to optically pump the NV centers so as to prepare the NV spins in an $m_s=0$ ground state.

11. The fluorescence detection system of claim 8, wherein the sample is formed of diamond material.

12. The fluorescence detection system of claim 11, wherein the color centers comprise NV (nitrogen vacancy) centers in the diamond material.

13. A fluorescence detection system comprising:
an optical source configured to generate excitation light;
a sample containing one or more fluorescence color centers that emit fluorescent light when irradiated with the excitation light from the optical source, wherein the sample has an index of refraction greater than its surrounding medium, said sample comprising at least one output face and further comprising at least two opposing faces configured to internally reflect the fluorescent light emitted by the one or more fluorescent color centers and optically guide the emitted fluorescent light to said at least one output face;
at least one optical detector configured to receive fluorescent light emitted through said at least one output face; and
a microwave source configured to manipulate electronic spin of the one or more fluorescent color centers;
wherein said at least one optical detector is positioned in contact with said at least one output face either directly or indirectly via a filter.

14. The fluorescence detection system of claim 13, wherein the sample is formed of diamond material.

15. The fluorescence detection system of claim 14, wherein the color centers comprise NV (nitrogen vacancy) centers in the diamond material.

16. A fluorescence detection system comprising:
an optical source configured to generate excitation light;
a sample containing one or more fluorescence color centers that emit fluorescent light when irradiated with the excitation light from the optical source, wherein the sample has an index of refraction greater than its surrounding medium, said sample comprising at least one output face and further comprising at least two opposing faces configured to internally reflect the fluorescent light emitted by the one or more fluorescent color centers and optically guide the emitted fluorescent light to said at least one output face;
at least one optical detector configured to receive fluorescent light emitted through said at least one output face; and
a microwave source configured to manipulate electronic spin of the one or more fluorescent color centers;
wherein the fluorescence detection system has a fluorescence collection efficiency of at least 30%.

17. The fluorescence detection system of claim 16, wherein the fluorescence detection system has a fluorescence collection efficiency between 50% and 90%.

18. The fluorescence detection system of claim 16, further comprising a processor configured to determine information about an external field based on the fluorescent light received by the at least one optical detector.

19. The fluorescence detection system of claim 18, wherein said external field is a magnetic field.

20. The fluorescence detection system of claim 18, wherein said external field is an electric field.

21. The fluorescence detection system of claim 16, wherein the sample is formed of diamond material.

22. The fluorescence detection system of claim 21, wherein the color centers comprise NV (nitrogen vacancy) centers in the diamond material.

23. A fluorescence detection system comprising:
an optical source configured to generate excitation light;
a sample containing one or more fluorescence color centers that emit fluorescent light when irradiated with the excitation light from the optical source, wherein the sample has an index of refraction greater than its surrounding medium, said sample comprising at least one output face and further comprising at least two opposing faces configured to internally reflect the fluorescent light emitted by the one or more fluorescent color centers and optically guide the emitted fluorescent light to said at least one output face;
at least one optical detector configured to receive fluorescent light emitted through said at least one output face; and
a microwave source configured to manipulate electronic spin of the one or more fluorescent color centers;
further comprising a processor configured to determine information about an external field based on the fluorescent light received by the at least one optical detector;
wherein said external field is a magnetic field, and
wherein the fluorescent detection system has a sensitivity better than $10 \text{ nT}/\sqrt{Hz}^{1/2}$.

24. The fluorescence detection system of claim 23, wherein the sample is formed of diamond material.

25. The fluorescence detection system of claim 24, wherein the color centers comprise NV (nitrogen vacancy) centers in the diamond material.

* * * * *